United States Patent [19]

Audousset et al.

[11] Patent Number: 6,106,577
[45] Date of Patent: Aug. 22, 2000

[54] USE OF A COMPOSITION CONTAINING A FILM-FORMING POLYMER DISPERSION AND NON-MELANIC PIGMENT FOR TEMPORARILY DYEING HUMAN OR ANIMAL HAIR

[75] Inventors: Marie-Pascale Audousset, Asnières; Jean Mondet, Aulnay-sous-boise, both of France

[73] Assignee: L'Oreal, Paris, France

[21] Appl. No.: 08/860,706

[22] PCT Filed: Nov. 7, 1996

[86] PCT No.: PCT/FR96/01754

§ 371 Date: Nov. 21, 1997

§ 102(e) Date: Nov. 21, 1997

[87] PCT Pub. No.: WO97/18795

PCT Pub. Date: May 29, 1997

[30] Foreign Application Priority Data

Nov. 23, 1995 [FR] France ................... 95 13940

[51] Int. Cl.$^7$ ............... D06P 5/13; A61K 7/13; C09B 67/20
[52] U.S. Cl. .............. 8/403; 8/405; 8/557; 8/637.1
[58] Field of Search ............... 8/405–435, 403, 8/557, 637.1

[56] References Cited

U.S. PATENT DOCUMENTS

| | | |
|---|---|---|
| 3,630,654 | 12/1971 | Rosenthal . |
| 3,928,273 | 12/1975 | Chang et al. . |
| 4,047,888 | 9/1977 | Papantoniou . |
| 4,394,479 | 7/1983 | Serlen . |
| 4,933,177 | 6/1990 | Grollier et al. . |
| 5,008,105 | 4/1991 | Grollier et al. . |
| 5,597,386 | 1/1997 | Igarashi et al. . |
| 5,735,907 | 4/1998 | Krustak et al. . |

FOREIGN PATENT DOCUMENTS

| | | |
|---|---|---|
| 379409 | 7/1990 | European Pat. Off. . |
| 9302655 | 2/1993 | European Pat. Off. . |
| 2312233 | 12/1976 | France . |
| 2323435 | 4/1977 | France . |
| 63-218613 | 9/1988 | Japan . |
| 3-197417 | 8/1991 | Japan . |
| 9413253 | 6/1994 | WIPO . |

OTHER PUBLICATIONS

English Derwent Abstract of EP–A–379409, Jul. 1990.
English Derwent Abstract of FR–A–2323435, Aug. 1977.

*Primary Examiner*—Margaret Einsmann
*Attorney, Agent, or Firm*—Finnegan, Henderson, Farabow, Garrett & Dunner, L.L.P.

[57] ABSTRACT

The present invention relates to the use, for the temporary dyeing of the hair or of animal hairs, of a composition comprising at least:

(a) an aqueous dispersion of particles of film-forming polymer containing at least one acidic function, in free or at least partially neutralized form, and (b) at least one pigment dispersed in the continuous phase of the said dispersion; the said pigment not resulting from the oxidative polymerization of an indole compound.

21 Claims, No Drawings

USE OF A COMPOSITION CONTAINING A FILM-FORMING POLYMER DISPERSION AND NON-MELANIC PIGMENT FOR TEMPORARILY DYEING HUMAN OR ANIMAL HAIR

The present invention relates to the use, for the temporary dyeing of the hair or animal hairs, of a composition comprising at least one aqueous dispersion of particles of film-forming polymer containing at least one acidic function, in which at least one non-melanin pigment is dispersed.

There are essentially three types of process known for dyeing the hair:
a) so-called permanent dyeing, the function of which is to produce a substantial change in the natural colour and which uses oxidation dyes that penetrate into the hair fibre and form the dye by a process of oxidative condensation;
b) semi-permanent or direct dyeing, which does not use the oxidative condensation process and withstands shampooing 4 or 5 times;
c) temporary or transient dyeing, which gives rise to a slight change in the natural colour of the hair, which holds from one shampoo-wash to the next and which serves to enhance or correct a shade that has already been obtained.

The invention proposes to use a dyeing process of the latter type leading to a coloration which can be eliminated at the first shampoo-wash. This may also be likened to a "make-up" process.

The term hair will be understood to refer to pilous systems consisting of a head of human hair and moustache or beard hairs.

In order to modify and enhance the hair temporarily, dyeing with direct dyes has already been proposed, but this dyeing may be heterogeneous on the parts of the hair which have been damaged by various degradations due to treatments such as, for example, permanent-waving, heat and atmospheric agents (sunshine, bad weather). Moreover, these dyes do not make it possible to obtain a natural and aesthetic grey shade except by using a mixture with other dyes, these having the drawback, however, of often being of different fastness to light and to shampooing, which may give rise to unsatisfactory final colorations.

It has also been proposed to use coloured polymers formed by grafting one or more dyes of azo, triphenylmethane, azine, indoamine or anthraquinone nature onto a polymer chain. These coloured polymers are not entirely satisfactory, in particular as regards the homogeneity of the coloration obtained or its fastness, not to mention the problems associated with their manufacture and in particular their reproducibility.

Application WO 93/02655 has also proposed a process for the temporary dyeing of keratin fibres using pigments resulting from the oxidative polymerization of indole derivatives such as 5,6-dihydroxyindole.

These melanin pigments may be combined with a film-forming latex in order to obtain better resistance to brushing and greater sheen.

This dyeing process leads to colorations whose results are not entirely satisfactory. The range of shades obtained is very limited. The properties relating to the dyeing power and to the remanence (resistance to water) are insufficient.

The Applicant has discovered, surprisingly, a process for so-called temporary dyeing, which may be eliminated at the first shampoo-wash, using a composition comprising an aqueous dispersion of particles of a film-forming polymer containing at least one acidic function and a pigment dispersed in the said dispersion which does not result from the oxidative polymerization of an indole compound. Such a process makes it possible to improve substantially the properties of remanence and of dyeing power. The range of colorations obtained by the process of the invention is substantially wider than that proposed by the process using melanin pigments. Furthermore, the colorations obtained by the dyeing process of the invention very appreciably withstand the rubbing of dry or wet hair with the user's fingers or hands or a cloth.

The subject of the present invention is thus the use, for the temporary dyeing of the hair or of animal hairs, of a composition comprising at least:
(a) an aqueous dispersion of particles of film-forming polymer containing at least one acidic function, in free or at least partially neutralized form, and
(b) at least one pigment dispersed in the continuous phase of the said dispersion; the said pigment not resulting from the oxidative polymerization of an indole compound.

The film-forming polymers containing at least one free or at least partially neutralized acidic function contain at least one acidic function of carboxylic, sulphonic, phosphoric or phosphonic type.

Their average molecular weight, preferably measured by steric exclusion chromatography, preferably ranges from 500 to 5,000,000.

The carboxylic acid group may be provided by at least one mono- or dicarboxylic acid monomer containing ethylenic unsaturation, such as those corresponding to the formula:

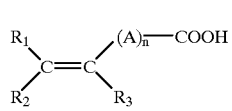

(I)

in which n is an integer from 0 to 10; A denotes a methylene group optionally connected to the carbon atom of the unsaturated group or to the neighbouring methylene group when n is greater than 1 via a hetero atom such as oxygen or sulphur or alternatively an aromatic ring such as phenyl or benzyl; $R_1$ denotes a hydrogen atom or a phenyl or benzyl group; $R_2$ denotes a hydrogen atom or a lower alkyl or carboxyl group; $R_3$ denotes a hydrogen atom, a lower alkyl group or a —$CH_2$—COOH, phenyl or benzyl group.

The film-forming polymers in accordance with the invention containing carboxylic acid groups are preferably chosen from the group consisting of:
A) Copolymers of (meth)acrylic acid and of at least one linear, branched or cyclic (cycloaliphatic or aromatic) (meth)acrylic acid ester monomer and/or of at least one linear, branched or cyclic (cycloaliphatic or aromatic) mono- or disubstituted (meth)acrylic acid amide monomer.

Mention may be made, by way of example, of:
acrylic acid/ethyl acrylate/N-tert-butylacrylamide terpolymers such as the product sold under the name Ultrahold 8 and that sold under the name Ultrahold Strong by the company BASF;
(meth)acrylic acid/tert-butyl (meth)acrylate and/or isobutyl (meth)acrylate/$C_1$–$C_4$alkyl (meth)acrylate copolymers such as the acrylic acid/tert-butyl acrylate/ethyl acrylate terpolymer sold by the company BASF under the name Luvimer 100P;
(meth)acrylic acid/ethyl acrylate/methyl methacrylate terpolymers and tetrapolymers such as the ethyl acrylate/methyl methacrylate/acrylic acid/methacrylic acid copolymer such as the product sold under the name Amerhold DR-25 by the company Amerchol;

methyl methacrylate/butyl or ethyl acrylate/hydroxyethyl or 2-hydroxypropyl acrylate or methacrylate/(meth)acrylic acid tetrapolymers such as the methyl methacrylate/butyl acrylate/hydroxyethyl methacrylate/methacrylic acid tetrapolymers sold by the company Rohm & Haas under the name Acudyne 255.

copolymers of acrylic acid and of $C_1$–$C_4$alkyl methacrylate and terpolymers of vinylpyrrolidone, of acrylic acid and of $C_1$–$C_{20}$alkyl, for example lauryl, methacrylate, such as that sold by the company ISP under the name Acrylidone M and the copolymer of methacrylic acid and of ethyl acrylate sold under the name Luvimer MAEX by the company BASF.

amphoteric copolymers such as N-octylacrylamide/methyl methacrylate/hydroxypropyl methacrylate/acrylic acid/tert-butylaminoethyl methacrylate copolymers, in particular that sold under the name Amphomer by the company National Starch, or the copolymer Lovocryl L47 sold by the same company.

copolymers of (meth)acrylic acid and of (meth)acrylic acid esters or amides furthermore containing linear, branched or cyclic (cycloaliphatic or aromatic, which may or may not be substituted) vinyl esters, such as vinyl acetate; vinyl propionate; vinyl esters of branched acid such as vinyl versatate; vinyl esters of substituted or unsubstituted benzoic acid; these copolymers may furthermore also contain groups resulting from the copolymerization with styrene, α- methylstyrene or a substituted styrene;

B) Copolymers of (meth)acrylic acid and of at least one olefinic monomer chosen from vinyl esters such as those mentioned above and containing no (meth)acrylic acid acrylamide or ester monomer. These copolymers may also contain olefinic groups resulting from the copolymerization with styrene, α-methylstyrene, a substituted styrene and optionally monoethylenic monomers such as ethylene.

C) Copolymers of vinyl monoacid such as crotonic acid and vinylbenzoic acid and/or of allylic monoacid such as allyloxyacetic acid.

By way of example, mention may be made of:

copolymers of crotonic acid containing vinyl acetate or propionate units in their chain and optionally of other monomers such as allylic or methallylic esters, vinyl ethers or vinyl esters of a saturated, linear or branched carboxylic acid containing a long hydrocarbon chain, such as those containing at least 5 carbon atoms, it being possible for these polymers optionally to be grafted and crosslinked, or alternatively a vinyl, allylic or methallylic ester of an α- or β-cyclic carboxylic acid. These copolymers may also contain olefinic groups resulting from the copolymerization with styrene, α-methylstyrene, a substituted styrene and optionally monoethylenic monomers such as ethylene.

Mention may be made more particularly of:

vinyl acetate/crotonic acid/polyethylene glycol copolymers such as that sold by the company Hoechst under the name "Aristoflex A"

vinyl acetate/crotonic acid copolymers such as that sold by the company BASF under the name "Luviset CA 66", vinyl acetate/crotonic acid/vinyl neodecanoate terpolymers such as that sold by the company National Starch under the name "Resine 28-29-30".

It is also possible according to the invention to use other types of film-forming polymers containing carboxyl acid functions, such as those described in French patent No. 78/30596 (2,439,798), having the general formula below:

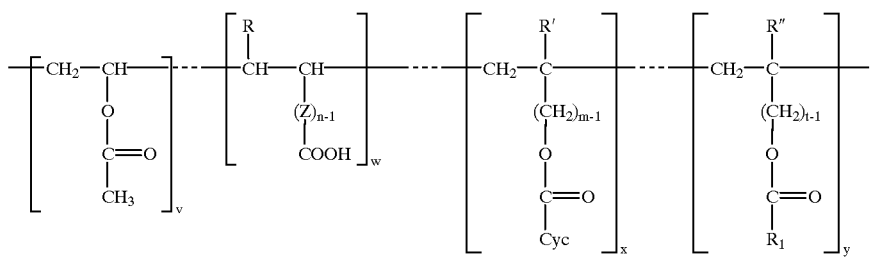

in which:

R, R' and R", which may be identical or different, represent a hydrogen atom or a methyl radical, m, n and t are 1 or 2, $R_1$ represents a saturated or unsaturated, linear or branched alkyl radical having from 2 to 21 carbon atoms, Z represents a divalent radical taken from the group consisting of: —$CH_2$—, —$CH_2$—O—$CH_2$— and —$CH_2$—O—$(CH_2)_2$—, Cyc represents a radical chosen from:

(i) a radical of formula:

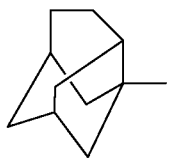

(ii) a radical of formula:

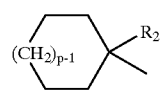

in which:

$R_2$ represents a hydrogen atom or a methyl radical, and p is 1 or 2, (iii) a radical of formula:

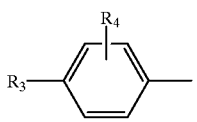

in which:
R$_3$ represents a hydrogen atom or a methyl, ethyl, tertbutyl, ethoxy, butoxy or dodecyloxy radical and R$_4$ represents a hydrogen atom, an alkyl radical of 1 to 4 carbon atoms or an alkoxy radical of 1 to 4 carbon atoms, and (iv) a radical of formula:

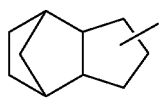

v represents from 10 to 91% and preferably from 36 to 84% by weight,
w represents from 3 to 20% and preferably from 6 to 12% by weight,
x represents from 4 to 60% and preferably from 6 to 40% by weight,
and y represents from 0 to 40% and preferably from 4 to 30% by weight,
v+w+x+y being equal to 100%.

Among these polymers, mention will preferably be made of the vinyl acetate/vinyl tert-butyl-benzoate/crotonic acid terpolymer with a weight composition of 65%/25%/10%.

D) Polymers derived from maleic, fumaric, citraconic or itaconic acid or anhydrides with monomers chosen from the group consisting of vinyl esters, vinyl ethers, vinyl halides, phenylvinyl derivatives, (meth)acrylic acid and esters thereof; these polymers may be monoesterified or monoamidated. Such polymers are described in particular in U.S. Pat. No. 2,047,398, 2,723,248 and 2,102,113 and GB patent 839,805, and in particular those sold under the names "Gantrez AN or ES" by the company ISP.

Polymers also forming part of this class are copolymers of maleic, citraconic or itaconic anhydrides and of an allylic or methallylic ester optionally containing an acrylamide or methacrylamide group, an α-olefin, acrylic or methacrylic esters, acrylic or methacrylic acids or vinylpyrrolidone in their chain, the anhydride functions are monoesterified or monoamidated. These polymers are described, for example, in French patents 2,350,384 and 2,357,241 from the Applicant.

Among these polymers, mention will be made more particularly of the methyl vinyl ether/maleic anhydride alternating copolymer (50/50 monoesterified with butanol and sold by the company ISP under the name Gantrez ES 425).

The film-forming polymers in accordance with the invention bearing sulphonic acid and/or sulphonate groups may be chosen from those obtained from vinyl-sulphonic acid, styrenesulphonic acid, 2-sulphoethyl methacrylate or acrylamido-2-methylpropanesulphonic acid.

These copolymers may be obtained by polymerization of at least one sulphonic acid group or a sulphonate group and of at least one monomer chosen from the group consisting of:
(i) linear, branched or cyclic vinyl esters;
(ii) linear, branched or cyclic (meth)acrylic acid esters;
(iii) mono- or disubstituted linear, branched or cyclic (meth)acrylic acid amides,
(iv) styrene, α-methylstyrene or substituted styrene.

According to the invention, the polymers which are particularly preferred are chosen from acrylic acid copolymers such as the acrylic acid/ethyl acrylate/N-tert-butylacrylamide terpolymer sold under the name "Ultrahold Strong" by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name "Résine 28-29-30" by the company National Starch, polymers derived from maleic, fumaric or itaconic acids or anhydrides with vinyl esters, vinyl ethers, vinyl halides, phenylvinyl derivatives or acrylic acid and esters thereof, such as the methyl vinyl ether/monoesterified maleic anhydride copolymer sold under the name "Gantrez ES 425" by the company ISP, the copolymers of methacrylic acid and of methyl methacrylate sold under the name "Eudragit L" by the company Rohm Pharma, the copolymer of methacrylic acid and of ethyl acrylate sold under the name "Luvimer Maex" by the company BASF, the vinylpyrrolidone/acrylic acid/lauryl methacrylate terpolymer sold under the name "Acrylidone LM" by the company ISP and the vinyl acetate/crotonic acid copolymer sold under the name "Luviset CA 66" by the company BASF and the vinyl acetate/crotonic acid/polyethylene glycol terpolymer sold under the name "Aristoflex A" by the company BASF, as well as the vinyl acetate/vinyl tert-butylbenzoate/crotonic acid terpolymer with a weight composition of 65%/25%/10%.

The aqueous dispersions of the polymers mentioned may be latices or pseudolatices. When they are in the form of latices, which are preferably at least partially neutralized, they result directly from the synthesis of the polymer by a well-known technique of emulsion polymerization. The degree of neutralization is such that the polymer remains in latex form and does not dissolve in the water.

They may also be in pseudolatex form. In this case, the polymer is already prepared and is then dispersed in water. The dispersion in water is self-stabilized by at least partial neutralization of the acid groups borne by the polymer.

The degree of neutralization of the film-forming polymers containing acidic functions should therefore be fully determined such that they remain insoluble in the water while at the same time being soluble in the organic solvent or solvents which may be present.

It goes without saying that the upper limit for the degree of neutralization which should not be exceeded in order for the polymer to remain insoluble in the water will depend on the nature of each film-forming polymer containing acidic functions. In general, this degree of neutralization is between 30 and 80% and preferably between 40 and 70% when the polymer has less than 2 meq/g of acidic functions and between 10 and 50%, preferably between 10 and 40%, when the polymer has more than 2 meq/g of acidic functions.

According to the invention, the acidic functions are neutralized using a non-volatile monobasic agent chosen, for example, from an inorganic base such as sodium hydroxide or potassium hydroxide or from an amino alcohol taken from the group consisting of 2-amino-2-methyl-1-propanol (AMP), triethanolamine, triisopropanolamine (TIPA), monoethanolamine, diethanolamine, tris[1-(2-hydroxy)propyl]amine, 2-amino-2-methyl-1,3-propanediol (AMPD) and 2-amino-2-hydroxymethyl-1,3-propanediol.

The pseudolatex of the cosmetic compositions according to the invention is obtained according to the known methods for the preparation of pseudolatices, with the proviso, however, of certain particular features which will be mentioned below.

The general process for the preparation of pseudolatices consists in dissolving a water-insoluble polymer in an organic solvent which is soluble or partially soluble in water, in dispersing the solution thus obtained in water with stirring and then in removing the organic solvent by evaporation under vacuum, which leads to a suspension consisting of polymer particles whose size is generally less than one μm.

According to this general process, the use of a surfactant, a mixture of surfactants or a protective colloidal polymer or alternatively of a surfactant/protective colloidal polymer mixture is essential in order to obtain good stabilization of the particles.

The film-forming polymers containing acidic functions as defined above cannot be used as they are in the preparation of pseudolatices but must be neutralized to a degree of neutralization of less than 100% in order to prevent them from dissolving fully in the water.

By partial neutralization of the polymers, it has been observed that it is possible to obtain pseudolatices that are particularly stable in the absence of hydrophilic stabilizer or of surfactant or alternatively of protective colloid.

In the preparation of the pseudolatex used in the compositions according to the invention, the acidic functions of the film-forming polymer are neutralized in situ in the solution of the polymer in the organic solvent by adding a determined amount of the non-volatile monobasic compound. The organic solvent used must be a volatile solvent or a mixture of such solvents having a boiling point below that of water and must be miscible or partially miscible with water.

The organic solvent as defined above is preferably chosen from acetone, methyl ethyl ketone, tetrahydrofuran, methyl acetate, ethyl acetate, isopropanol and ethanol.

After obtaining the solution of the partially neutralized polymer in the organic solvent, an emulsion is then prepared by pouring, with stirring, an appropriate amount of water optionally containing an anti-foaming agent, whose role will be to facilitate the subsequent evaporation of the organic phase, into the organic solution obtained.

According to a variant of the process as defined above, the acidic functions of the polymer dissolved in the organic solvent may be neutralized during formation of the emulsion by pouring in an aqueous solution containing the required amount of the non-volatile monobasic compound.

During the formation of the emulsion, the stirring is preferably carried out using a shearing disperser of the Moritz or Ultra-Turrax or Raineri type equipped with defloc-culating blades.

The emulsion thus obtained is particularly stable without it being necessary to use a surfactant, insofar as the acidic groups of the polymer place themselves at the interface with the water and protect the droplets from coalescing by electrostatic repulsion.

After formation of the emulsion at a temperature between room temperature and about 70° C., the organic solvent is then evaporated off under reduced pressure until it has been totally removed, the evaporation preferably being carried out with gentle heating.

A pseudolatex is thus obtained, that is to say an aqueous dispersion of particles of the film-forming polymer, which is free of any surfactant or other hydrophilic stabilizer while at the same time being very stable, which is particularly advantageous in hair cosmetics.

The average size of the particles of the film-forming polymer is preferably less than 500 nm and more preferably between 10 and 350 nm and more particularly less than 250 nm.

The size polydispersity of the particles, measured by quasielastic light scattering, is generally between 0.1 and 0.40 and preferably less than 0.35.

The film-forming polymers containing acidic groups in accordance with the invention are present in the compositions in concentrations preferably ranging from 5 to 40% by weight of active material and more particularly from 8 to 25% by weight relative to the total weight of the composition.

The pigments in accordance with the invention are chosen from any cosmetically or dermatologically acceptable organic or inorganic pigment which does not result from the oxidative polymerization of indole compounds.

They may be in the form of powder or pigmentary paste.

Among the inorganic pigments, mention may be made, by way of example, of titanium dioxide (rutile or anatase) optionally surface-treated and classified in the Color Index under the reference CI77891; black, yellow, red and brown iron oxides classified under the references CI77499, 77492 and 77491; manganese violet (CI77742); ultramarine blue (CI77007); chromium oxide hydrate (CI77289); ferric blue (CI77510).

Among the organic pigments, mention may be made, by way of example, of the pigment Yellow 3 sold in particular under the trade name "Jaune Covanor W 1603" by the company Wacker (CI17710), "D & C Red No. 19" (CI45170), "D & C Red No. 9" (CI15585), "D & C Red No. 21" (CI45380), "D & C Orange No. 4" (CI15510), "D & C Orange No. 5" (CI45370), "D & C Red No. 27" (CI45410), "D & C Red No. 13" (CI15630), "D & C Red No. 7" (CI15850-1), "D & C Red No. 6" (CI15850-2), "D & C Yellow No. 5" (CI19140), "D & C Red No. 36" (CI12085), "D & C Orange No. 10" (CI45425), "D & C Yellow No. 6" (CI15985), "D & C Red No. 30" (CI73360), "D & C Red No. 3" (CI45430), carbon black (CI77266) and lakes based on cochineal carmine (CI75470).

It is also possible to use pearlescent pigments which may be chosen in particular from white pearlescent pigments such as mica coated with titanium oxide or bismuth oxide; coloured pearlescent pigments such as titanium mica with iron oxides, titanium mica with ferric blue or with chromium oxide, titanium mica with an organic pigment of precipitated type, as well as those based on bismuth oxychloride.

Pigmentary pastes of an organic pigment are used more particularly, such as the products sold by the company Hoechst under the name:

| | |
|---|---|
| Jaune Cosmenyl 10G | Pigment Yellow 3 (CI11710) |
| Jaune Cosmenyl G | Pigment Yellow 1 (CI11680) |
| Orange Cosmenyl GR | Pigment Orange 43 (CI71105) |
| Rouge Cosmenyl R° | Pigment Red 4 (CI12085) |
| Carmine Cosmenyl FB | Pigment Red 5 (CI12490) |
| Violet Cosmenyl RL | Pigment Violet 23 (CI51319) |
| Bleu Cosmenyl A2R | Pigment Blue 15.1 (CI74260) |
| Vert Cosmenyl GG | Pigment Green 7 (CI74260) |
| Noir Cosmenyl R | Pigment Black 7 (CI77266) |

The pigments are present in concentrations preferably ranging from 0.05 to 10% by weight and more particularly from 0.1 to 3% by weight relative to the total weight of the composition.

The pH of the compositions in accordance with the invention preferably ranges from 6 to 8 and more particularly from 6 to 7.5.

In order to improve, if necessary, the properties of the film formed by the composition based on an aqueous dispersion of film-forming polymer containing acidic groups and insoluble pigment, at least one plasticizer is preferably added to the said dispersion.

In the case of a latex, the plasticizer or plasticizers is(are) added to the polymer particle dispersion which is already made up.

In the case of an aqueous dispersion in pseudolatex form, the plasticizer or plasticizers may be added to the dispersion once the pseudolatex has been formed or during the dispersing of the polymer.

The plasticizers used in accordance with the present invention may be of hydrophilic or hydrophobic (or sparingly hydrophilic) nature or mixtures consisting of a hydrophilic plasticizer and a hydrophobic plasticizer.

They are generally present in the compositions of the invention in concentrations ranging is from 0.1 to 80% by weight and preferably 5 to 40% by weight relative to the weight of the film-forming polymer containing acidic groups.

Among the hydrophilic plasticizers, mention may be made of glycol ethers and, in particular:

the Carbitols from the company Union Carbide, namely Carbitol or diethylene glycol ethyl ether, methyl Carbitol or diethylene glycol methyl ether and butyl Carbitol or diethylene glycol butyl ether, the Cellosolves from the company Union Carbide, namely Cellosolve or ethylene glycol ethyl ether, butyl Cellosolve or ethylene glycol butyl ether and hexyl Cellosolve or ethylene glycol hexyl ether, the Dowanols from the company Dow Chemical and in particular Dowanol PM or propylene glycol methyl ether, Dowanol DPM or dipropylene glycol methyl ether, Dowanol TPM or tripropylene glycol methyl ether or alternatively Dowanol DM or diethylene glycol methyl ether.

As other hydrophilic plasticizers, mention may also be made of:

castor oil oxyethylenated with 40 mol of ethylene oxide, such as that sold under the name "Mulgofen LE 716";

propylene glycol;

butyl glycol;

propylene glycol monopropyl ether sold by the company Union Carbide under the name "Propyl Propasol";

propylene glycol mono-tert-butyl ether sold by the company Arco under the name "Acrosolv PEB";

ethylene glycol monomethyl ether acetate, propylene glycol monomethyl ether acetate sold (as regards the latter) by the company Dow under the name "Dowanol PMA", dipropylene glycol methyl ether acetate sold by the company Dow under the name "Dowanol DPMA".

As hydrophobic or very sparingly hydrophilic plasticizers, mention may be made of:

propylene glycol ethers such as:

propylene glycol phenyl ether sold by the company Dow under the name "Dowanol PPH";

dipropylene glycol monobutyl ether sold by the company Dow under the name "Dowanol DPnB";

tripropylene glycol monobutyl ether sold by the company Dow under the name "Dowanol TPnB";

tripropylene glycol isobutyl ether sold by the company Dow under the name "Dowanol TPIB";

propylene glycol monobutyl ether sold by the company Dow under the name "Dowanol PnB".

ether esters of propylene glycol and of ethylene glycol, such as:

ethylene glycol butyl ether acetate;

propylene glycol n-butyl ether acetate sold by the company Dow under the name "Dowanol PmBA".

diacid esters such as:

diethyl, dibutyl and diisopropyl phthalates and adipates;

diethyl and dibutyl tartrates;

diethyl and dibutyl succinates;

diethyl and dibutyl sebacates;

diethyl, dibutyl and 2-diethylhexyl phosphates;

diethyl or dibutyl acetyl citrate;

glycerol esters such as glyceryl diacetate (diacetin) and glyceryl triacetate (triacetin).

One particular form of the composition according to the invention consists of a composition containing a plasticizer system consisting of a mixture of at least two plasticizers of differing rate of evaporation; (1) one of them, the "permanent" one, having a high boiling point (preferably above 200° C.), (2) the other, the "temporary" one, being more volatile than (1) and needing to evaporate after water. The first plasticizer (1) makes it possible to ensure the permanent plasticization of the polymer, whereas the second plasticizer (2) makes it possible to aid the coalescence of the particles and to accelerate the film-formation (coalescence agent).

The proportion of "permanent" plasticizer (1) depends on the material of the polymer used, in particular on the glass transition of the polymer used and on the intrinsic glass transition of the plasticizer. The proportion is such that the glass transition of the polymer plasticized with the permanent plasticizer is between 10° C. and 40° C. and preferably between 15° C. and 30° C., which usually corresponds, depending on the polymer chosen, to an amount ranging from 2 g/100 g of polymer to 30 g/100 g of polymer.

The proportion of "temporary" plasticizer (2), also known as coalescence agent, which is present occasionally only to promote the film-formation of the latex or of the pseudolatex, may range from 2 g/100 g of polymer to 15 g/100 g of polymer.

The compositions used for the temporary dyeing of the hair or of the animal hairs may be in various forms, such as relatively thickened liquids, creams or gels.

The compositions according to the invention which are intended to be used for temporary dyeing may also contain various adjuvants that are commonly used in hair compositions. Among these adjuvants, mention may be made of volatile or non-volatile, insoluble or soluble silicones in the form of oils, gums, resins or powders, nonionic, anionic, cationic or amphoteric polymers; quaternized or non-quaternized proteins; sunscreens; surfactants; anti-foaming agents; hydrating agents; wetting agents; emollients; synthetic or plant oils; preserving agents, sequestering agents; antioxidants; fragrances; basifying or acidifying agents, agents for placing the pigments in suspension; thickeners.

Another subject of the invention is a process for the temporary dyeing of the hair or of animal hairs, characterized in that a composition as defined above is applied in an effective amount to the hair or to the animal hairs.

The examples which follow serve to illustrate the invention without being limiting in nature.

EXAMPLES

Example 1

| | | |
|---|---|---|
| Organic pigment sold under the name Carmine Cosmenyl (CI12790) by the company Hoechst | 2.5 g | |
| Pseudolatex of vinyl acetate/crotonic acid/vinyl 4-t-butylbenzoate (65/10/25) copolymer prepared according to the process described in application FR 2,697,160 | 15 g | AM |
| Diisopropyl adipate (plasticizer) | 3.75 g | |

| -continued | | |
|---|---|---|
| 2-Amino-2-methyl-1-propanol (agent for neutralizing the polymer) | | 0.495 g |
| Water | qs | 100 g |

The dye composition is applied to dry hair, in an amount of 4 g per 3 g of hair. It is left to dry at room temperature.

A red coloration is obtained. The hair feels soft and non-sticky. No discharge on dry or wet hair is observed.

Example 2

| | | |
|---|---|---|
| Organic pigment sold under the name Bleu Cosmenyl (CI74260) by the company Hoechst | | 3.0 g |
| Pseudolatex of vinyl acetate/crotonic acid/vinyl 4-t-butylbenzoate (65/10/25) copolymer prepared according to the process described in application FR 2,697,160 | | 15 g AM |
| Diisopropyl adipate (plasticizer) | | 3.75 g |
| 2-Amino-2-methyl-1-propanol (agent for neutralizing the polymer) | | 0.495 g |
| Water | qs | 100 g |

The composition is applied under the same conditions as in Example 1.

A blue coloration is obtained. The hair does not feel sticky and there is no discharge on dry or wet hair.

Example 3

| | | |
|---|---|---|
| Black pigmentary paste sold under the name Copidis (CI77266) by the company Hoechst | | 1.2 g AM |
| Pseudolatex of vinyl acetate/crotonic acid/vinyl 4-t-butylbenzoate (65/10/25) copolymer prepared according to the process described in application FR 2,697,160 | | 10 g AM |
| Diisopropyl adipate (plasticizer) | | 1 g |
| 2-Amino-2-methyl-1-propanol (agent for neutralizing the polymer) | | 0.62 g |
| Butyl glycol | | 1 g |
| Water | qs | 100 g |

The dye composition is applied to dry hair, in an amount of 3 g per 1.5 g of hair. It is left to dry at room temperature. A black coloration is obtained.

COMPARATIVE EXAMPLE A
(counter-type of Example 2):

| | | |
|---|---|---|
| Bleu Cosmenyl A2R (pigment) | | 3 g |

| -continued | | |
|---|---|---|
| Cationic polymer in pseudolatex form as defined below | | 15 g AM |
| Water | qs | 100 g |

The composition is applied under the same conditions as in Example 1. The hair feels sticky and considerable discharge is observed on dry and wet hair, in contrast with Example 2.

The cationic polymer in pseudolatex form has the theoretical structure:

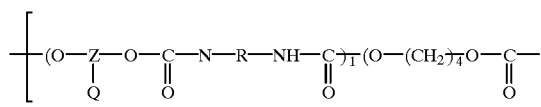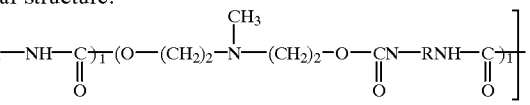

where R denotes:

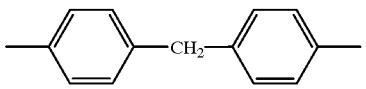

where Z is a trivalent radical
Q is a polysiloxane segment.

The polycondensate corresponds to the reaction between:
1 mol of X 22176 DX sold by Shin Etsu (polysiloxane oligomer of molecular weight 4000 and of OH number 26.4) and of formula:

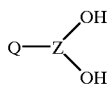

1 mol of 1,4-butanediol (coupler);
2 mol of 4,4'-diphenylmethane diisocyanate (referred to hereinbelow as MDI).

A solution of 100 g of oligomer X 22176 DX in 120 g of tetrahydrofuran (referred to hereinbelow as THF) is introduced, under a stream of nitrogen, into a cylindrical reactor fitted with a central stirrer of the anchor type, a thermometer, a condenser, a vacuum inlet and an inlet for bubbling nitrogen through, and over which is mounted an addition flask. Several vacuum/nitrogen degassing cycles are carried out in order to purge the air from inside the reactor. Stirring is carried out at about 250 revolutions/minute. 17.9 g of solid MDI are then introduced rapidly, and under a stream of nitrogen, into the medium with stirring at room temperature.

After dissolving fully with stirring, the mixture is heated at 65° C. (boiling of the solvent) for 3 hours.

A solution of a mixture of couplers consisting of the following is then introduced into the medium at 650C with stirring:
   2.145 g of 1,4-butanediol
   2.84 g of N-methyldiethanolamine (MEA)
   200 g of THF
The mixture is left to react for one hour at 65° C.

A solution of 4.82 g of 1,4-butanediol in 50 g of THF is then added rapidly (via the addition flask). The mixture is left to react with stirring for one hour at 65° C.

0.05 g of pure dibutyltin laurate catalyst (liquid) is then added and the mixture is left to react at 65° C. for eight hours. At this stage, the coupling reaction is complete.

The medium is cooled to room temperature. The synthetic solution is purified by precipitation from an ethanol/water mixture (70/30 by weight). The precipitate is recovered and dried.

455 g of the above synthetic solution containing 27% polymer (i.e. 123 g of polymer) are introduced into a beaker. This solution is stirred vigorously using an Ultra Turrax machine. A solution consisting of the following is introduced portionwise into the medium with stirring:

11.6 g of 2M HCl 50 ml of deionized water (to neutralize the polymer to 100% according to its amine content)

500 g of deionized water are then added, still with vigorous stirring.

The emulsion obtained is then concentrated on a rotary evaporator in order to remove the organic synthesis solvent (THF) completely and to concentrate the water.

A pseudolatex with a final solids content of 27% is thus obtained, having the following characteristics:

average particle size: 100 nm, size polydispersity: 0.14

COMPARATIVE EXAMPLE B (counter-type of Example 3):

| | | |
|---|---|---|
| Melanin pigment resulting from the oxidation of 5,6-dihydroxyindole with aqueous hydrogen peroxide solution in ammoniacal medium | | 1.2 g |
| Pseudolatex of vinyl acetate/crotonic acid/vinyl 4-t-butylbenzoate (65/10/25) copolymer prepared according to the process described in application FR 2,697,160 | | 10 g AM |
| Diisopropyl adipate (plasticizer) | | 1 g |
| 2-Amino-2-methyl-1-propanol (agent for neutralizing the polymer) | | 0.62 g |
| Butyl glycol | | 1 g |
| Water | qs | 100 g |

1-Comparative Tests on the Dyeing Power

The increase in dye obtained on natural or permanent-waved hair with this formulation A is compared with that obtained with Example 3 according to the invention. Compositions A and 3 are applied, under the same conditions, to natural hair containing 90% white hairs and to permanent-waved hair containing 90% white hairs, in a proportion of 3 g per 1.5 g of hair. The compositions are then left to dry at room temperature.

The shade of the hair for dyeing and the shade of the hair dyed by each of the test formulations is measured according to the Munsell notation, using the parameters H, V and C. The increase in dye obtained is determined by the variation in colour $\Delta E_1$, calculated according to the Nickerson formula below:

$$\Delta E_1 = 0.4 C_0 \Delta H + 6 \Delta V + 3 \Delta C$$

The higher the value of $\Delta E_1$, the greater is the increase in dye obtained.

The results of the tests of increase in dye are shown in Table 1 below.

TABLE 1

| HAIR TESTED | SHADE MEASURED ACCORDING TO THE MUNSELL NOTATION | $\Delta E_1$ |
|---|---|---|
| Non-dyed natural white | 4.4Y 5.9/1.7 | — |
| Non-dyed permanent-waved white | 4.0Y 5.5/1.4 | — |
| Permanent-waved white dyed with formulation B | 3.5Y 4.3/1.0 | 12.3 |
| Permanent-waved white dyed with formulation B | 2.2Y 3.8/0.9 | 12.7 |
| Natural white dyed with formulation 3 of the invention | 5.0Y 3.4/0.4 | 19.3 |
| Permanent-waved white dyed with formulation 3 of the invention | 3.6Y 3.0/0.4 | 18.2 |

It is observed that the formulation of Example 3 containing a non-melanin pigment leads to more intense colorations than those obtained with counter-type formulation B containing a melanin pigment.

2-Comparative Tests on the Remanence to Water

The relative variation in the degradation of the coloration observed after immersing in water natural hair or permanent-waved hair dyed with formulation B or with Example 3 according to the invention is studied.

The compositions B and the formulation of Example 3 are applied under the same conditions, onto natural hair containing 90% white hairs and onto permanent-waved hair containing 90% white hairs, in a proportion of 3 g per 1.5 g of hair. The compositions are left to dry at room temperature.

The shade of the hair for dyeing and the shade of the hair dyed by each of the test formulations is measured according to the Munsell notation, using the parameters H, V and C. The increase in dye $\Delta E_1$ is determined. The values of $\Delta E_1$ are shown in Table 1 above.

1.5 g of hair dyed with each of the formulations B and 3 is then immersed in 100 g of cold water for 3 minutes, after which it is left to dry at room temperature.

The shade of hair thus treated is again measured according to the Munsell notation, using the parameters H, V and C. The variation in their coloration $\Delta E_2$ is calculated according to the Nickerson formula defined above.

The relative variation in the degradation of the coloration on natural dyed hair or on permanent-waved dyed hair is determined as percentages by the ratio $\Delta E_2 / \Delta E_1$. The greater this variation, the lower is the remanence to water of the coloration.

The results of the tests of remanence to water are shown in Table 2 below.

TABLE 2

| DYED HAIR DAMAGED BY IMMERSION IN COLD WATER | SHADE MEASURED ACCORDING TO THE MUNSELL NOTATION AFTER IMMERSION IN COLD WATER | % OF DEGRADATION OF THE COLOR $\Delta E_2 / \Delta E_1$ |
|---|---|---|
| Permanent-waved white dyed with formulation B | 3.2Y 4.8/1.1 | 27.8% |
| Permanent-waved white dyed with formulation B | 1.6Y 4.2/1.1 | 7.9% |
| Natural white dyed with formulation 3 of the invention | 4.9Y 3.6/0.5 | 25.3% |

TABLE 2-continued

| DYED HAIR DAMAGED BY IMMERSION IN COLD WATER | SHADE MEASURED ACCORDING TO THE MUNSELL NOTATION AFTER IMMERSION IN COLD WATER | % OF DEGRADATION OF THE COLOR $\Delta E_2/\Delta E_1$ |
|---|---|---|
| Permanent-waved white dyed with formulation 3 of the invention | 3.0Y 2.8/0.5 | 8.8% |

It is observed that the formulation of Example 3 containing a non-melanin pigment is of better remanence to water than the counter-type formulation B containing a melanin pigment.

What is claimed is:

1. A composition comprising:
   (a) an aqueous dispersion of particles of at least one film-forming polymer containing at least one acidic function, said acidic function being in free or partially neutralized form, wherein said at least one film-forming polymer is a polymer containing a sulphonic acid or sulphonate function obtained by the copolymerization of at least one sulphonic acid or sulphonate group with at least one monomer selected from:
      (i) linear, branched, or cyclic vinyl esters;
      (ii) linear, branched, or cyclic (meth)acrylic acid esters;
      (iii) mono- or di-substituted linear, branched, or cyclic (meth)acrylic acid acrylamides; and
      (iv) styrene, α- methylstyrene or a substituted styrene, and
   (b) at least one pigment dispersed in the aqueous dispersion, wherein the pigment is not formed by oxidative polymerization of an indole compound, wherein the composition is a temporary hair dye for animal or human hair.

2. The composition according to claim 1, wherein the average molecular weight of the film-forming polymer, measured by steric exclusion chromatography, ranges from 500 to 5,000,000.

3. The composition according to claim 1, wherein the aqueous dispersion of particles of the film-forming polymer is in latex or pseudolatex form.

4. The composition according to claim 1, wherein the degree of neutralization of the acidic functions ranges from 30 to 80% when the film-forming polymer contains less than 2 meq/g of acidic function and ranges from 10 to 50% when the film-forming polymer contains more than 2 meq/g of acidic function.

5. The composition according to claim 1, wherein the acidic function is at least partially neutralized with an inorganic base or an amino alcohol.

6. The composition according to claim 1, wherein the average size of the particles of the film-forming polymer is less than or equal to 500 nm.

7. The composition according to claim 6, wherein the average size of the particles of the film-forming polymer ranges from 10 to 350 nm.

8. The composition according to claim 1, wherein the size polydispersity of the particles of film-forming polymer, measured by quasielastic light scattering, ranges from 0.1 to 0.4.

9. The composition according to claim 1, wherein the film-forming polymer is present in a concentration ranging from 5 to 40% by weight relative to the total weight of the composition.

10. The composition according to claim 1, wherein the pigment is inorganic or organic and is in the form of a powder or pigmentary paste.

11. The composition according to claim 1, wherein the pigment is present in a concentration ranging from 0.05 to 10% by weight relative to the total weight of the composition.

12. The composition according to claim 1, wherein the aqueous dispersion further contains at least one plasticizer.

13. The composition according to claim 12, wherein the plasticizer is hydrophilic, hydrophobic, sparingly hydrophilic or a mixture of a hydrophilic plasticizer and a hydrophobic or sparingly hydrophilic plasticizer.

14. The composition according to claim 12, wherein the at least one plasticizer is present in a concentration ranging from 0.1 to 80% by weight, relative to the weight of the film-forming polymer.

15. The composition according to claim 14, wherein the at least one plasticizer is present in a concentration ranging from 5 to 40% by weight, relative to the weight of the film-forming polymer.

16. The composition according to claim 12, wherein the at least one plasticizer is a plasticizer system comprising:
   (1) a plasticizer having a boiling point above 200° C., and
   (2) a plasticizer which is more volatile than plasticizer (1) and is less volatile than water.

17. The composition according to claim 16, wherein plasticizer (1) is present in a concentration ranging from 2 to 30 g per 100 g of film-forming polymer and plasticizer (2) is present in a concentration ranging from 2 to 15 g per 100 g of film-forming polymer.

18. The composition according to claim 1, which is in the form of a thick liquid, a cream or a gel.

19. The composition according to claim 1, which further comprises at least one additive selected from:
   volatile or non-volatile, soluble or non-soluble silicones in the form of oils, gums, resins or powders; nonionic, anionic, cationic or amphoteric polymers; quaternized or non-quaternized proteins; anti-foaming agents; hydrating agents; wetting agents; emollients; synthetic or plant oils; preserving agents; sequestering agents; antioxidants; fragrances; basifying agents; acidifying agents; suspending agents; and thickeners.

20. A process for the temporary dyeing of human hair, said process comprising applying an effective amount of the composition according to claim 1 to the human hair.

21. A process for the temporary dyeing of animal hairs, said process comprising applying an effective amount of the composition according to claim 1 to the animal hairs.

* * * * *